(12) United States Patent
Chatelier et al.

(10) Patent No.: US 8,221,994 B2
(45) Date of Patent: Jul. 17, 2012

(54) ADHESIVE COMPOSITION FOR USE IN AN IMMUNOSENSOR

(75) Inventors: Ronald C. Chatelier, Bayswater (AU); Dennis Rylatt, Wheelers Hill (AU)

(73) Assignee: Cilag GmbH International (CH)

( * ) Notice: Subject to any disclaimer, the term of this patent is extended or adjusted under 35 U.S.C. 154(b) by 409 days.

(21) Appl. No.: 12/570,268

(22) Filed: Sep. 30, 2009

(65) Prior Publication Data

US 2011/0073493 A1    Mar. 31, 2011

(51) Int. Cl.
*G01N 27/327* (2006.01)

(52) U.S. Cl. ............ 435/7.72; 204/403.02; 204/403.14; 436/514

(58) Field of Classification Search ............ 204/403.01–403.15; 435/7.1–7.95; 436/512–514, 518–542
See application file for complete search history.

(56) References Cited

U.S. PATENT DOCUMENTS

| | | |
|---|---|---|
| 3,692,733 A | 9/1972 | Kasagi et al. |
| 5,942,102 A | 8/1999 | Hodges et al. |
| 6,174,420 B1 | 1/2001 | Hodges et al. |
| 6,379,513 B1 | 4/2002 | Chambers et al. |
| 6,475,360 B1 | 11/2002 | Hodges et al. |
| 6,521,110 B1 | 2/2003 | Hodges et al. |
| 6,632,349 B1 | 10/2003 | Hodges et al. |
| 6,638,415 B1 | 10/2003 | Hodges et al. |
| 6,881,378 B1 | 4/2005 | Zimmer et al. |
| 6,946,067 B2 | 9/2005 | Hodges et al. |
| 7,043,821 B2 | 5/2006 | Hodges |
| 7,431,820 B2 | 10/2008 | Hodges |
| 2003/0180814 A1 | 9/2003 | Hodges et al. |
| 2004/0203137 A1 | 10/2004 | Hodges et al. |
| 2006/0134713 A1 | 6/2006 | Rylatt et al. |
| 2010/0006452 A1 | 1/2010 | Hodges et al. |

FOREIGN PATENT DOCUMENTS

| | | |
|---|---|---|
| EP | 1389633 | 2/2004 |
| JP | 2007-139781 | 6/2007 |
| WO | WO 01/02093 A3 | 1/2001 |
| WO | WO 2005/051542 A1 | 6/2005 |
| WO | 2005083412 A1 | 9/2005 |
| WO | 2006074137 | 7/2006 |
| WO | 2008135564 A2 | 11/2008 |

OTHER PUBLICATIONS

European Search Report for Application No. 10251678.8 dated Jan. 3, 2011, 4 pages.
Japanese Office Action for JP Application No. 2010-217520; dated Mar. 15, 2012; 2 pages.

*Primary Examiner* — J. Christopher Ball
(74) *Attorney, Agent, or Firm* — Hiscock & Barclay, LLP

(57) ABSTRACT

An adhesive composition for use in devices and methods for measuring a presence or a concentration of a particular component, such as an antigen, in a sample, such as blood, are provided. In one exemplary embodiment of an adhesive composition, the composition includes an adhesive, water, a poloxamer, and an anticoagulant. The adhesive can include particular properties, such as being hydrophilic, pressure-sensitive, heat-activated, and/or water soluble. The adhesive is particularly useful because it can help improve the flow of sample a device. For example, when the device is an immunosensor, the adhesive can help prevent the blood from clotting in chambers of the immunosensor. This results in a more efficient and accurate determination of the concentration of the sample. Methods of making the composition and device in which the composition can be used are provided, as are methods of using the same.

8 Claims, 2 Drawing Sheets

ADHESIVE COMPOSITION FOR USE IN AN IMMUNOSENSOR

FIELD

The present disclosure relates to adhesive compositions for use in blood contacting devices, such as an immunosensor, and methods for measuring a concentration of a component associated with a sample, such as an antigen in a blood sample.

BACKGROUND

Analyte detection in physiological fluids, e.g. blood or blood derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include glucose for diabetes management, cholesterol, and the like. In response to this growing importance of analyte detection, a variety of analyte detection protocols and devices for both clinical and home use have been developed.

One type of device used to detect and analyze blood samples are immunosensors. Immunosensors generally include a plurality of electrodes and chambers that are configured to receive and analyze a sample. The different chambers of the immunosensor serve different purposes. For example, a fill chamber of an immunosensor can be configured to receive a sample, a reaction chamber can be configured to react the sample with an antibody disposed in the immunosensor, and a detection chamber can be configured to detect the presence or concentration of a protein or antigen within the sample following the reaction with the sample and the antibody. The various components of the immunosensor can be fabricated by using, for example, a combination of substrates, plastics, laminates, and adhesives.

Conventional adhesives are used to bond materials like the substrates and the plastics together. This can be accomplished, for example, by coating the adhesive on the substrate, laminating the adhesive, and then bonding the laminated adhesive-substrate combination with the plastic layer. Conventional adhesives are generally hydrophobic so that they can maintain their bond in a wet environment. This, however, is a detriment to the flow of liquid because liquid flow can be impeded by the hydrophobic properties of the adhesive. Thus, it can often be difficult for blood samples to move between various chambers of an immunosensor. In particular, there can be a tendency for the sample to clot within the immunosensor, thereby blocking movement of the sample through the immunosensor. This can result in undesirable complications, errors, and delays in analyzing the sample.

Accordingly, it would be desirable to improve the flow of blood through an immunosensor, as well as improve the accuracy and speed of measurements taken with an immunosensor.

SUMMARY

Devices and methods are generally provided for measuring a presence or a concentration of a certain material within a sample. Adhesive compositions for use in such devices and methods are also provided. In one embodiment of an adhesive composition for use in an immunosensor, the composition includes an adhesive, water, a poloxamer, and an anticoagulant. The adhesive and the water can be combined to form a mixture prior to being included with the poloxamer and the anticoagulant. The adhesive can have a number of different properties associated with it, including being pressure-sensitive, heat-activated, and water soluble. In one embodiment the adhesive is a sulfopolyester. The anticoagulant can be selected from a group that includes heparin, citrate, ethylenediaminetetraacetic acid, and oxalate. The poloxamer can include units derived from ethylene oxide and propylene oxide. In one embodiment the ethylene oxide and propylene oxide serve as monomers in block copolymers. A concentration of the poloxamer with respect to the adhesive can be approximately in the range of about 0.05 to about 0.5 percent. In an embodiment in which the anticoagulant is heparin, a concentration of the heparin with respect to the adhesive can be approximately in the range of about 0.1 to about 10 milligrams per milliliter.

One exemplary embodiment of an immunosensor can include a lower electrode, an upper electrode, and a separator disposed therebetween. The immunosensor can also include a plurality of chambers, including a reaction chamber, a detection chamber, and a fill chamber. The reaction and detection chambers can each be formed in the separator, while the fill chamber can be formed at least partially in the separator and one of the lower and upper electrodes. The fill chamber can be spaced a distance apart from the detection chamber, overlapping at least a portion of the reaction chamber. Further, a vent can be formed at least partially in each of the separator, the lower electrode, and the upper electrode. The vent can be spaced a distance apart from the reaction chamber, overlapping at least a portion of the detection chamber. A hydrophilic adhesive tape can be coupled to one of the lower and upper electrodes and disposed over the vent, while a sealing component can be coupled to the other of the lower and upper electrodes and also disposed over the vent. The hydrophilic adhesive tape and the sealing component can be made from one or more of the same materials, including entirely of the same material(s), or alternatively, can be made from one or more different materials. The hydrophilic adhesive tape can form a wall of the fill chamber, and further, can have an anticoagulant incorporated therein.

The lower electrode can have a first reagent in liquid form and a second reagent in liquid form disposed thereon. The first liquid reagent can include an antibody conjugated to an enzyme in a buffer, while the second liquid reagent can include ferricyanide, a substrate for the enzyme, and an electrochemical mediator in a dilute acid solution. The first and second liquid reagents can be striped on the lower electrode and dried. The upper electrode can have magnetic beads conjugated to an antigen striped and dried thereon. The immunosensor can be constructed such that the reaction chamber has the first reagent of the lower electrode and the magnetic beads conjugated to the antigen of the upper electrode disposed therein and the detection chamber has the second reagent of the lower electrode disposed therein.

The enzyme of the first liquid reagent of the lower electrode of the immunosensor can be glucose dehydrogenase-PQQ and the buffer in which the enzyme can be located can include citraconate, sucrose, poloxamers, and calcium ions. The second liquid reagent of the lower electrode of the immunosensor can include ferricyanide, glucose, and phenazine ethosulfate in a dilute citraconic acid solution. In one embodiment the anticoagulant of the adhesive tape can be heparin. A concentration of the heparin with respect to a concentration of the hydrophilic adhesive can be approximately in the range of about 0.1 to about 10 milligrams per milliliter. The immunosensor can further include a meter disposed below the reaction chamber. In one exemplary embodiment the meter can contain a magnet. The meter can be configured to apply a potential between the lower and upper electrodes, as well as measure a resulting current. In one embodiment a heating element can be associated with the meter. In another embodiment the meter can include a piercing component that is configured to pierce at least one of the hydrophilic tape and the sealing component disposed over the vent.

One method for measuring a blood sample can include providing a reaction chamber and a detection chamber that are formed in a separator disposed between two electrodes. Further, a fill chamber that is at least partially formed in the separator and one of the two electrodes can also be provided. The fill chamber can be spaced a distance apart from the detection chamber and can overlap at least a portion of the reaction chamber. Still further, a vent that is at least partially formed in the separator and the two electrodes can be provided. The vent can be spaced a distance apart from the reaction chamber and can overlap at least a portion of the detection chamber. The method can further include providing an antibody-enzyme conjugate in a first buffer and magnetic beads linked to an antigen in a second buffer in the reaction chamber, and providing ferricyanide, glucose, and a mediator in a dilute acid in the detection chamber. A first seal can be provided over a first side of the vent by way of a hydrophilic adhesive tape. The tape can also form a wall of the fill chamber. A second seal can be provided over a second side of the vent by way of a sealing component.

The method can further include providing a blood sample to the fill chamber such that at least a portion of the blood sample moves from the fill chamber to the reaction chamber. The vent can be opened after a pre-determined time, for instance, by piercing at least one of the hydrophilic adhesive tape and the sealing component. Opening the vent after a pre-determined time can allow portions of the blood sample containing the antibody-enzyme conjugate that is not bound to the magnetic beads to move to the detection chamber. Oxidation of the glucose in the detection chamber can be catalyzed, which can result in the formation of ferrocyanide. The method can also include applying a potential between the two electrodes, electrochemically detecting a current from the ferrocyanide, and calculating a concentration of the antigen in the blood sample based on the signal detected.

In some embodiments of the method, the two electrodes can be heated. In one embodiment the hydrophilic adhesive of the hydrophilic adhesive tape can include heparin. A concentration of heparin with respect to a concentration of the hydrophilic adhesive can be approximately 1 milligram per milliliter. In another embodiment the hydrophilic adhesive can include a poloxamer.

BRIEF DESCRIPTION OF DRAWINGS

This invention will be more fully understood from the following detailed description taken in conjunction with the accompanying drawings, in which.

DETAILED DESCRIPTION

Figure 1:
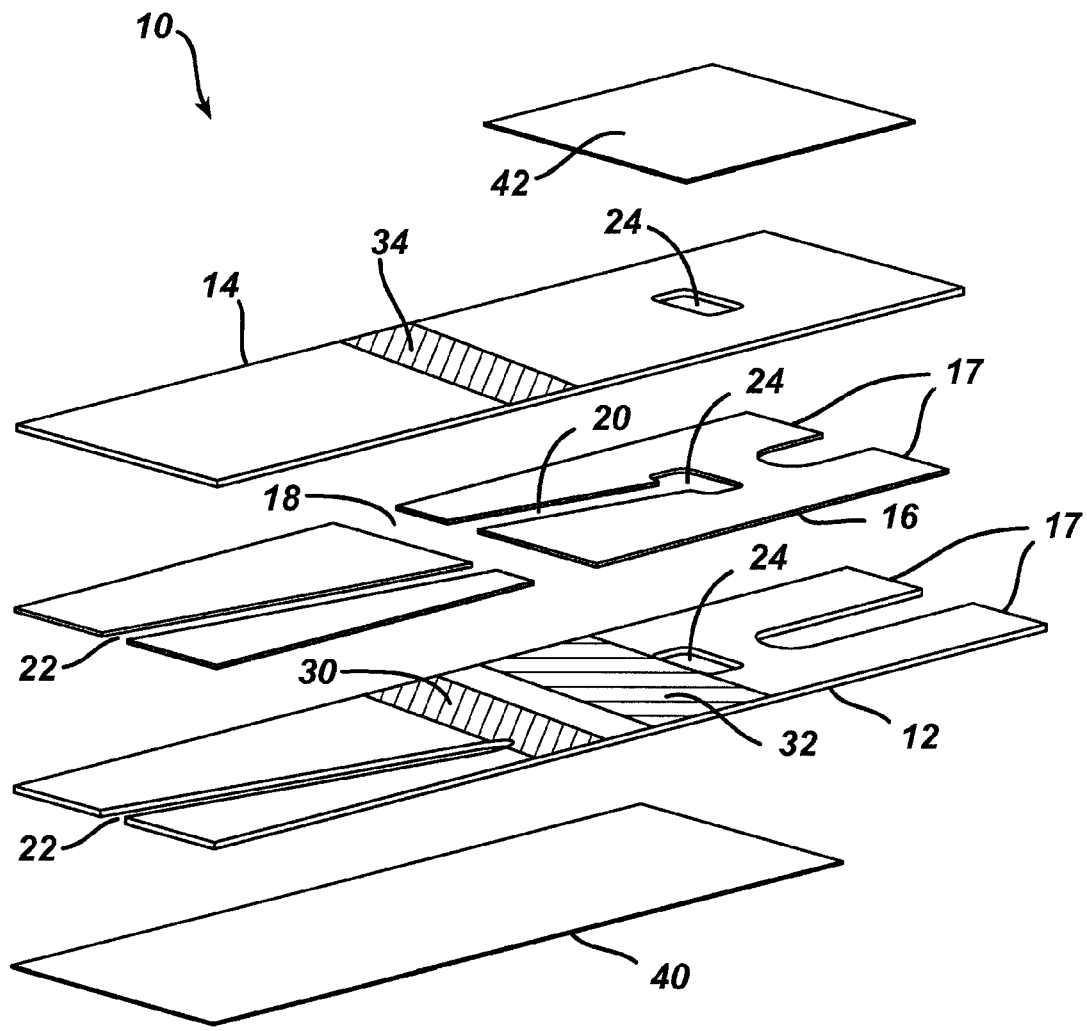
FIG. 1 is an exploded view of one exemplary embodiment of an immunosensor in accordance with the present invention.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The subject compositions, devices, and methods are suitable for use in the determination of a wide variety of analytes in a wide variety of samples, and are particularly suited for use in the determination of analytes in whole blood, plasma, serum, interstitial fluid, or derivatives thereof. The compositions of the present invention can include any number of components in a variety of amounts and concentrations. One having skill in the art will recognize that components, amounts, and concentrations discussed herein are merely examples for use in the present inventions and that a variety of other combinations to form one or more compositions can be achieved in the spirit of the present disclosure.

Similarly, the compositions can be used in conjunction with a variety of different devices. Thus, to the extent compositions are discussed for use with an immunosensor generally, the compositions can also be used in any number of devices, for instance, by way of non-limiting example, electrochemical cells, electrochemical sensors, hemoglobin sensors, antioxidant sensors, and biosensors. Non-limiting examples of some of the types of devices with which the adhesive compositions can be used are discussed in greater detail in U.S. Pat. No. 5,942,102 of Hodges et al., entitled "Electrochemical Method" and filed on May 7, 1997, U.S. Pat. No. 6,174,420 of Hodges et al., entitled "Electrochemical Cell" and filed on May 18, 1999, U.S. Pat. No. 6,379,513 of Chambers et al., entitled "Sensor Connection Means" and filed on Sep. 20, 1999, U.S. Pat. No. 6,475,360 of Hodges et al., entitled "Heated Electrochemical Cell" and filed on Sep. 11, 2000, U.S. Pat. No. 6,632,349 of Hodges et al, entitled "Hemoglobin Sensor" and filed on Jul. 14, 2000, U.S. Pat. No. 6,638,415 of Hodges et al., entitled "Antioxidant Sensor" and filed on Jul. 14, 2000, U.S. Pat. No. 6,946,067 of Hodges et al., entitled "Method of Forming an Electrical Connection Between an Electrochemical Cell and a Meter" and filed on Dec. 9, 2002, U.S. Pat. No. 7,043,821 of Hodges, entitled "Method of Preventing Short Sampling of a Capillary or Wicking Fill Device" and filed on Apr. 3, 2003, and U.S. Pat. No. 7,431,820 of Hodges et al., entitled "Electrochemical Cell" and filed on Oct. 1, 2002, each of which is incorporated by reference in its entirety.

Likewise, to the extent compositions are discussed for use with a device having a particular configuration, any number of configurations can be used. For example, some configurations that can be used with the present disclosures include sensors having two electrodes facing each other, sensors having two electrodes on the same plane, and sensors having three electrodes, two of which are opposed and two of which are on the same plane. These different configurations can occur in any number of devices, including the aforementioned devices.

Still further, the methods discussed herein, such as those related to forming compositions, constructing devices, and using devices, are also not limited by the particular steps or order of the steps. One having skill in the art will recognize various orders in which the methods can be performed, and further, will recognize that steps can be modified or added without departing from the sprit of the invention.

In one exemplary embodiment of a composition for use in an immunosensor, the composition includes an adhesive, water, a poloxamer, and an anticoagulant. The adhesive can have a variety of properties associated with it in addition to being adhesive. These properties can result from properties associated with the particular adhesive that is used in the composition, or alternatively, they can result from the addition of other components to the composition to assist in creating or enhancing the properties. The adhesive can be hydrophilic for example, thereby allowing it to interact well with water and other liquids. In such embodiments the adhesive can remain well-wet, which can result in allowing liquid samples to more easily flow through devices with which the composition is associated. One way of achieving an adhesive having hydrophilic properties is by blending a hydrophilic, hemocompatible polymer into the adhesive. When devices that include an adhesive that improves flow are used in conjunction with blood samples, the use of such adhesive can reduce the amount of clotting that occurs within the device. Improving flow can also speed up the time of various reactions associated with such devices. For example, in an immunosensor, a composition that includes an adhesive that improves the flow of the sample can decrease the time it takes for an antigen-antibody reaction to occur. This is because a liquid sample that fills a biosensor slowly can tend to dissolve the dried reagent and "push" it along the fill path. In turn, regions of electrode that are depleted of the reagent can be left behind, thus reducing the rate of the reaction.

The flow of fluid through devices associated with the composition can also be improved by making the adhesive water soluble. Such a property also helps the adhesive remain well-wet, and further, because it helps improve the flow, the other aforementioned benefits that result from an improved flow also result from a water soluble adhesive. Further, a water soluble adhesive can help prevent the release of volatile organic compounds or toxic components when the adhesive is applied to a surface of devices such as immunosensors.

The adhesive can also be made pressure-sensitive and/or heat-activated. By making the adhesive pressure-sensitive and/or heat-activated, the device with which the adhesive is associated with can be more easily processed. For example, the adhesive, and thereby the portion of the device with which the adhesive is associated, may not adhere strongly to cutting tools used to manufacture the device when the adhesive is made to be heat-activated.

While a number of different adhesives can be used in conjunction with the present composition, in one exemplary embodiment the adhesive is a sulfopolyester. Other polyesters can also be used, such as polyesters and sulfopolyesters from the Eastman AQ™ polymer line.

Water associated with a composition can have its typical form and can be associated with other components of the composition at any desired time. Filtered water, pure water, tap water, and treated water are all examples of types of water that can be used in an adhesive composition. In an exemplary embodiment the water can be substantially free of dissolved ions to allow an adhesive to more easily interact with the water. This can occur because ions can help prevent the adhesive from dissolving. In one exemplary embodiment the adhesive and the water are mixed together to form a mixture. When the adhesive includes properties such as being hydrophilic and/or water soluble, the resulting mixture can be easy to mix with other components of the adhesive composition, such as poloxamers and anticoagulants.

One or more poloxamers, which are sometimes referred to by their trade name Pluronics®, can be included as part of an adhesive composition to assist in making the composition hydrophilic. The one or more poloxamers can be block copolymers, e.g., nonionic tri-block copolymers, that can be derived from and can include both polyoxypropylene, which is sometimes referred to as polypropylene oxide), and polyoxyethylene, which is sometimes referred to as poly(ethylene oxide). Propylene oxide and ethylene oxide can serve as monomers in the block copolymers.

The lengths of the blocks of the copolymers can be adjusted to create a wide variety of different poloxamers, each having different properties based on the particular composition of each of the poloxamers. The poloxamers can be blended into the adhesive directly or into the composition generally. Because many adhesives are hydrophobic, the use of poloxamers can enhance the performance of the adhesive composition. The ethylene oxide and propylene oxide polymer blocks can have a variety of chemical structures to allow available poloxamers to exhibit various ranges of desirable and undesirable characteristics. For example, some poloxamers work better to help fill an immunosensor with blood because they can help counteract the effects of high haematocrit blood. BASF Pluronic® L 62 (also known as PE 6200) and BASF Pluronic® F 87 Prill are just two examples of poloxamers that can assist in allowing an immunosensor to be filled with blood because of its ability to make the composition hydrophilic.

An adhesive composition can also include one or more anticoagulants. The inclusion of anticoagulants can help reduce the risk of a liquid, such as blood, from clotting in a device in which the composition is used. Further, anticoagulants can provide for more consistent fill behavior when trying to fill a device with a liquid and/or when the liquid tries to move between various chambers in the device. The speed and extent of a sample fill can be better controlled by including an anticoagulant in the composition. The anticoagulant can be blended into an adhesive directly or it can be blended into the composition generally. The anticoagulant can create surfaces that leach anticoagulant into a sample as the sample fills the device. While many types of anticoagulants can be used, some exemplary materials include heparin (including sodium heparin and lithium heparin), citrate, ethylenediaminetetraacetic acid (sometimes referred to as EDTA), and oxalate.

The formation of an adhesive composition can be carried out in any number of ways. The methods discussed herein are merely examples of ways in which the various components can be combined to form one version of the adhesive composition. In view of the present disclosure, a person having ordinary skill in the art will recognize that the amounts of the components included in the adhesive composition, which can include an adhesive(s), water, a poloxamer(s), and an anticoagulant(s), can be delicately balanced in order to achieve a workable solution. For example, a composition that contains too much of an adhesive can prevent a sample from properly filling an immunosensor. Further, a composition that contains too much of a poloxamer can cause the sample to not want to de-wet, leading to the sample not flowing between the chambers of the immunosensor. Likewise, a composition that contains too little of a poloxamer can cause the sample to not wet at all and can lead to undesired clotting of the sample within the chambers of the immunosensor. Still further, a composition that contains too much of an anticoagulant can adversely affect the sample. For instance, when the sample is blood, too much of an anticoagulant can adversely affect the red blood cells of the sample. Accordingly, the particular balance of the components used to form the adhesive composition can be important to improving the performance of the immunosensor.

In one exemplary embodiment of forming an adhesive composition, an adhesive and water are combined and mixed together to form a mixture of the same. For example, approximately 4.5 kg of Eastman AQ™ 2150, which is a sulphonated poly(ethylene)terephthalate, can be combined with approximately 13.5 L of pure water. The water can be substantially free of dissolved ions so that dissolution of the adhesive is enhanced. The Eastman AQ™ 2150 can be substantially made from a water-dispersible sulfopolyester having a small number of modifiers and additives. After forming the adhesive-water mixture, the mixture can be heated and then stored. For example, the mixture can be placed in an oven heated to approximately 140° F. for a period of about four days. It can be stirred for a period of approximately five to ten minutes each day. Subsequently, the mixture can be stored at approximately 46° F. or less, which can help reduce microbial growth.

Either before mixing the adhesive with water or after the mixture is formed, one or more poloxamers can be mixed in. For example, BASF Pluronic® L 62 can be mixed in a manner such that the final concentration of the poloxamer is approximately in the range of about 0.05 to about 0.5 percent. In one exemplary embodiment the poloxamer represents approximately 0.1 percent of the composition. Similarly, either before mixing the adhesive with water or after the mixture is formed, one or more anticoagulants can be mixed in. In one exemplary embodiment the anticoagulant(s) is mixed in after the poloxamer(s) is mixed in. Continuing the adhesive composition example from above, following the addition of the BASF Pluronic® L 62, sodium heparin can be mixed in a manner such that the final concentration of the heparin compared to the composition is approximately in the range of about 0.1, to about 10 mg/mL. In one exemplary embodiment the concentration of the heparin compared to the concentration of the composition is approximately 1 mg/mL. One type of sodium heparin that can be used with the present composition is Sigma Aldrich porcine mucosa heparin, which can have a concentration of approximately 172 units/mg. Together, the combination of the adhesive (e.g., 4.5 kg of Eastman AQ™ 2150), the water (e.g., 13.5 L pure water), the poloxamer (e.g., BASF Pluronic® L 62 at a concentration of approximately 0.1% with respect to the composition as a whole), and the anticoagulant (e.g., Sigma Aldrich porcine mucosa heparin at approximately 172 units/mg and combined to form a concentration as a whole of approximately 1 mg/mL) can form an exemplary adhesive composition.

The adhesive compositions that result from the present disclosures can be used in a variety of different devices. The type of device with which they can be used can affect in what form the compositions will be used. In some embodiments the composition may be applied directly to a device, for example by painting it directly onto an electrode, while in other embodiments it may first be painted onto a sheet before the sheet with the composition disposed thereon is associated with the device with which it will be used. In one exemplary embodiment the adhesive composition can be coated on a sheet of biaxially-oriented polyethylene terephthalate, which can sometimes be referred to as Mylar, to form an adhesive tape. The composition can be applied to such a sheet in a variety of ways, for example it can be applied using a K-bar. Other methods for applying the composition to a sheet include, but are not limited to, slot-head coating and curtain coating.

The adhesive compositions that result from the present disclosures are also not limited to use with devices that measure various aspects of blood. Rather, the adhesive compositions can be used in a variety of manners in which adhesives compositions can be useful. By way of non-limiting example, the adhesive compositions that result from the present disclosures can be used in treating wounds, for example, by incorporating the adhesive composition into a bandage. The components of the adhesive composition, which are discussed in greater detail below, can be balanced to create the desired effect for use on an adhesive bandage. The results of using the adhesive compositions on an adhesive bandage can include improved clotting by the adhesive bandage and a reduction in tissue damage and/or pain when removing the adhesive bandage from a wound. Other uses of the adhesive composition in place of standard adhesives are also contemplated by the disclosures herein.

An immunosensor is one of the many types of devices with which the adhesive compositions of the present disclosure can be used. Immunosensors are generally configured to receive and analyze a sample, such as blood. While the adhesive compositions of the present disclosure can be used with immunosensors having any number of configurations, in one exemplary embodiment the immunosensor can include lower and upper electrodes with a separator disposed therebetween. The lower and upper electrodes can be used interchangeably as the working and counter or counter/reference electrodes. In fact, because voltage applied to the immunosensor can be flipped and/or alternated, each of the lower and upper electrodes can serve as the working electrode and the counter or counter/reference electrode at different stages. For ease of description purposes, in the present application the lower electrode will be considered the working electrode and the upper electrode the counter or counter/reference electrode.

A plurality of chambers can be formed within the immunosensor in portions of at least one of the lower electrode, the upper electrode, and the separator. Examples of chambers that can be included are a fill chamber, by which a sample can be introduced into the immunosensor, a reaction chamber, by which a sample can be reacted with one or more desired materials, and a detection chamber, by which a concentration of a particular component of the sample can be determined. The immunosensor can also include a vent hole to allow air to enter and escape the immunosensor as desired, an adhesive tape to selectively seal one side of the vent hole, and an additional sealing component to selectively seal a second side of the vent hole. The adhesive tape can also form a wall of the fill chamber.

As illustrated in FIG. 1, in one embodiment of an immunosensor 10, the immunosensor 10 includes a lower electrode 12 having two liquid reagents 30, 32 striped onto it. The lower electrode 12 can be formed using any number of techniques used to form electrodes, but in one embodiment a polyethylene terephthalate (PET) sheet that is filled with barium sulphate is sputter-coated with gold. Other non-limiting example of forming an electrode are disclosed in U.S. Pat. No. 6,521, 110 of Hodges et al., entitled "Electrochemical Cell" and filed on Nov. 10, 2000, the contents of which is incorporated by reference in its entirety. Likewise, the liquid reagents 30, 32 can have a number of different compositions, but in one embodiment the first liquid reagent 30 includes an antibody conjugated to an enzyme, such as GDH-PQQ, in a buffer that contains sucrose, as well as Pluronics® (i.e., a poloxamer), citraconate (i.e., an anticoagulant), and calcium ions, while the second liquid reagent 32 includes a mixture of ferricyanide, glucose, and a second mediator, such as phenazine ethosulfate, in an acidic buffer, such as a dilute citraconic acid solution. The first and second liquid reagents 30, 32 can be dried onto the lower electrode 12. A number of techniques can be used to dry the reagents 30, 32, but in one embodiment, following the striping of the reagents 30, 32 on the lower electrode 12, one or more infrared dryers can be applied to the reagents 30, 32. One or more air dryers can also be used, for example, subsequent to the infrared dryers. References to a first reagent and a first liquid reagent and a second reagent and a second liquid reagent herein are used interchangeably and are not necessarily an indication that the reagents are in their liquid or dried form at a given time for a particular embodiment. Further, some of the components associated with the first and second liquid reagents can be used interchangeably and/or in both the first and second liquid reagents as desired. By way of non-limiting example, an anticoagulant can be associated with either or both of the first liquid reagent 20 and the second liquid reagent 32.

A line can be formed in the sputter-coated gold between the reagents 30, 32 such that an edge of one of the reagents 30, 32 is very close to, or touches, the line. The line can be applied using laser ablation or with a sharp metal edge. In one exemplary embodiment the line can be applied before the reagents 30, 32 are striped on the electrode. The line can be designed to electrically insulate the section of the lower electrode 12 under the detection chamber from the section that will be under the reaction chamber. This can provide a better definition of an area of the working electrode during the electrochemical assay.

The immunosensor 10 can also include an upper electrode 14 having one or more magnetic beads 34 containing surface-bound antigens thereon. The antigens can be configured to react with the antibody disposed on the lower electrode 12 and the sample within a reaction chamber 18, as described in further detail below. One having skill in the art will recognize that the components disposed on the lower electrode 12 and on the upper electrode 14 can be interchangeable. Thus, the lower electrode 12 can include one or more magnetic beads 34 and the upper electrode 14 can include two liquid reagents 30, 32 striped onto it. Further, although in the illustrated embodiment the length of the electrode 12 forms the length of the entire body of the immunosensor 10, in other embodiments the electrode can be only a portion of a layer of an immunosensor that serves as the lower or upper electrode or multiple electrodes can be disposed on a single layer of an immunosensor.

A separator 16 disposed between the lower and upper electrodes 12, 14 can have a variety of shapes and sizes, but it generally is configured to desirably engage the lower and upper electrodes 12, 14 to form the immunosensor 10. In one exemplary embodiment the separator 16 is adhesive on both sides, although the adhesive associated with the separator 16 can be separate from the adhesive composition used in conjunction with the immunosensor 10 as described in further detail below. The separator 16 can further include a release liner on each side of the two sides of the separator 16. The separator 16 can be cut in a manner that forms at least two cavities. A first cavity can be formed to serve as a reaction chamber 18 and a second cavity can be formed to serve as a detection chamber 20. In one embodiment the separator 16 can be kiss-cut such that the reaction chamber 18 is aligned with the electrodes 12, 14 to allow an antigen-antibody reaction therein while the detection chamber 20 is aligned with the electrodes 12, 14 to allow for the electrochemical determination of ferrocyanide therein.

In one embodiment the separator 16 can be placed on the lower electrode 12 in a manner that allows the magnetic beads 34 of the upper electrode 14 and the first reagent 30 of the lower electrode 12 to be at least partially disposed in the reaction chamber 18 and the ferricyanide-glucose combination of the second reagent 32 of the lower electrode 12 to be at least partially disposed in the detection chamber 20. It can be advantageous to include an anticoagulant in each of the first and second liquid reagents 30, 32 so that an anticoagulant is associated with each of the reaction and detection chambers 18, 20. In some embodiments, the combination of one of the upper and lower electrodes 12, 14 and the separator 16 can be laminated together to form a bi-laminate, while in other embodiments the combination of each of the lower electrode 12, the upper electrode 14, and the separator 16 can be laminated together to form a tri-laminate. It is within the spirit of the invention, however, to include additional layers as desired.

A fill chamber 22 can be formed by punching a hole into one of the lower and upper electrodes 12, 14 and the separator 16. In the illustrated embodiment the fill chamber is formed by punching a hole in the lower electrode 12 and the separator 16 such that the hole in the lower electrode 12 overlaps the reaction chamber 18. As shown, the fill chamber 22 can be a distance apart from the detection chamber 20. Such a configuration allows a sample to enter the immunosensor 10 through the fill chamber 22 and flow into the reaction chamber 18 to be reacted, for example with the first liquid reagent 30 that includes the antibody conjugated to an enzyme in a buffer on the first electrode 12 and the magnetic beads 34 striped on the upper electrode 14, without entering the detection chamber 20. Once the sample has been reacted, it can then flow into the detection chamber 20 for interaction with the second liquid reagent 32, for example the mixture of ferricyanide, glucose, and the second mediator in an acidic buffer.

A vent 24 can be formed by punching a hole through each of the two electrodes 12, 14 and the separator 16 such that the vent 24 extends through the entirety of the immunosensor 10. The hole can be punched in a number of different locations, but in one exemplary embodiment it can overlap a region of the detection chamber 20 that is spaced apart from the reaction chamber 18.

The vent 24 can be sealed in a number of different manners using a number of different sealing components, but in the illustrated embodiment a first side of the vent 24 located on the lower electrode 12 is sealed using a hydrophilic adhesive tape 40 that includes the adhesive composition of the present invention and a second side of the vent 24 located on the upper electrode 14 is sealed using a sealing component, such as Scotch® tape 42. The adhesive tape 40 can be formed in a variety of manners, including by being coated on a sheet of biaxially-oriented polyethylene terephthalate, as discussed above. The adhesive sides of both the adhesive tape 40 and the Scotch® tape 42 can both face the immunosensor 10. As shown, not only can the adhesive tape 40 form a seal for the vent 24, but it can also form a wall for the fill chamber 22 so that the sample can be contained therein. In embodiments in which the adhesive tape 40 includes the adhesive composition of the present disclosure, the properties of the adhesive tape 40 can thus be associated with the fill chamber 22. Accordingly, a surface of the fill chamber 22 can be hydrophilic and/or water soluble, thereby allowing it to remain well-wet when the sample is disposed therein. Both the adhesive tape 40 and the Scotch® tape can be selectively associated and disassociated with the immunosensor 10 to provide venting and/or sealing for the immunosensor 10 and the components disposed therein as desired. One having skill in the art will recognize that Scotch® tape 42 is just one example of a sealing component, and that many other types of components capable of sealing the vent 24 can also be used, including the hydrophilic adhesive tape 40.

Figure 2:
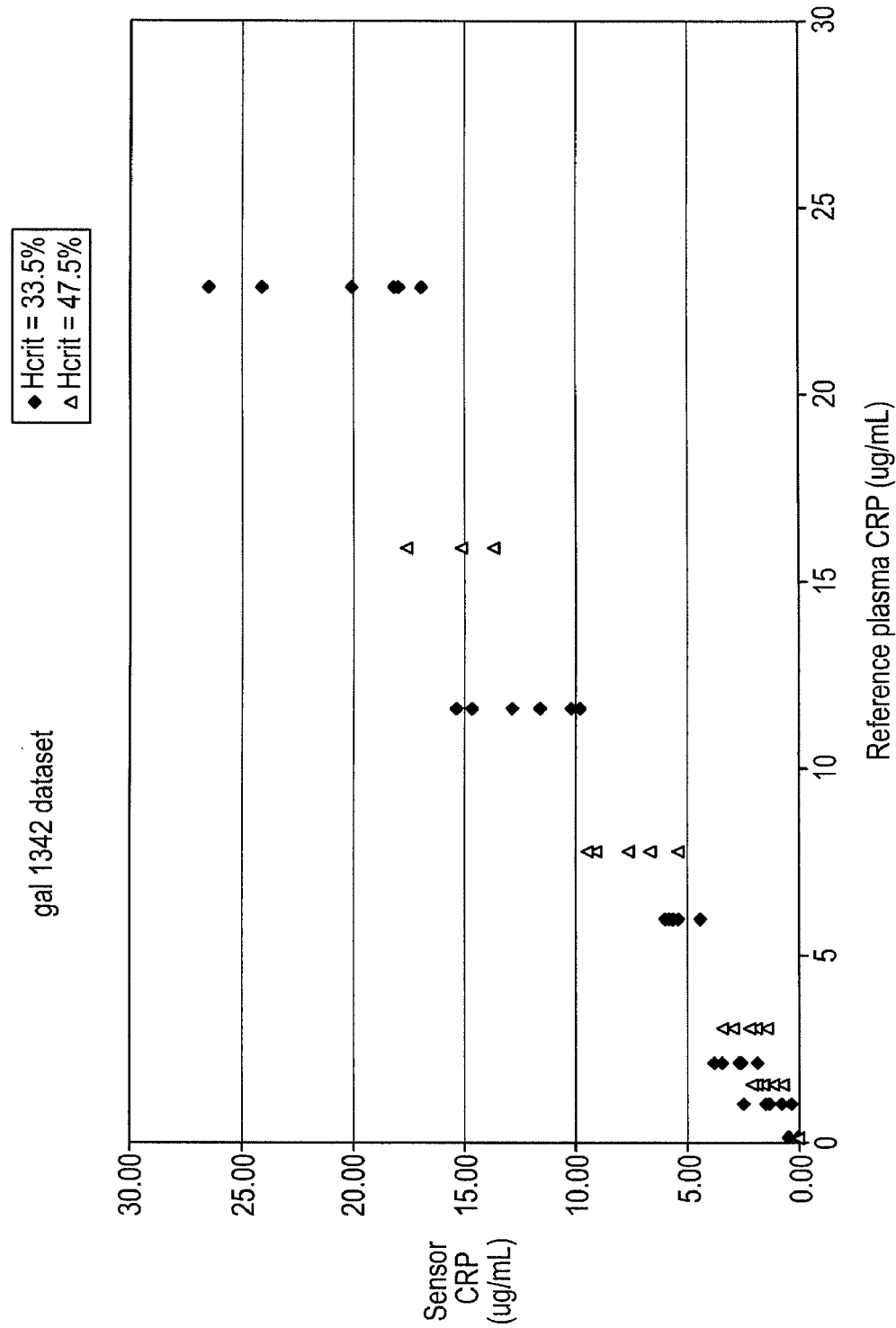
FIG. 2 is a chart illustrating a measurement of C-reactive proteins using an immunosensor in accordance with the present invention.

The advantage of using an anticoagulant, such as heparin, as part of the adhesive composition are illustrated by the chart of FIG. 2. The inclusion of heparin in one embodiment of an adhesive composition improved the ability of the immunosensor to more easily function with blood over a wide range of clinically relevant hematocrits. As shown, a measurement of C-reactive proteins for both a hematocrit of 33.5% and 47.5% show that the concentration of the reference plasma and the actually sensed concentration are relatively consistent over a data set. Perfectly ideal results would form a straight line with the concentration of C-reactive protein measured by the meter equaling the reference concentration of C-reactive protein for each data point. The actual data results are either near such a theoretical line, or to the extent they are spaced from such a line, the data points are generally equidistant from both sides of the line, indicating that with large sample sizes the results would also likely approach the theoretical line. Thus, the present invention results in immunosensors that are generally accurate.

While the present disclosure discusses a variety of different embodiments related to immunosensors in which the adhesive compositions discussed herein can be used, other embodiments of immunosensors can also be used with the adhesive compositions of the present disclosure. Non-limiting examples of such embodiments include those described in U.S. Patent Application Publication No. 2003/0180814 of Hodges et al., entitled "Direct Immunosensor Assay" and filed on Mar. 21, 2002, U.S. Patent Application Publication No. 2004/0203137 of Hodges et al., entitled "Immunosensor" and filed on Apr. 22, 2004, U.S. Patent Application Publication No. 2006/0134713 of Rylatt et al., entitled "Biosensor Apparatus and Methods of Use" and filed on Nov. 21, 2005, and U.S. patent application Ser. No. 12/563,091, which claims priority to each of U.S. Patent Application Publication Nos. 2003/0180814 and 2004/0203137, each of which is incorporated by reference in its entirety.

In one embodiment the immunosensor 10 can be configured to be placed into a meter that is configured to apply a potential to the electrodes 12, 14 and measure a current that results from the application of the potential. The meter can include a number of different features. For example, the meter can include a magnet that is configured to maintain certain components of the immunosensor 10 in one chamber while other components flow to the other. In one exemplary embodiment the magnet of the meter is located such that, upon placing the immunosensor 10 in the meter, the magnet is disposed below the reaction chamber 18. This can allow the magnet to assist in holding back any magnetic beads 34, and more particularly any antibody-enzyme conjugate that is bound to the beads 34, from flowing into the detection chamber 20. Another optional feature of the meter is a heating element. A heating element can help speed up the reaction rate and help the sample flow through the immunosensor 10 in a desired manner by reducing the viscosity. As described in greater detail below, a piercing instrument can also be associated with the meter.

In use, the immunosensor 10 can determine a concentration of an antigen of a sample. The immunosensor 10 can be connected to a meter. The sample containing the antigen to be determined can be loaded into the immunosensor 10 by placing it into the fill chamber 22 of the immunosensor 10. The sample can be placed using a variety of techniques, but in one exemplary embodiment a drop of blood from a fingertip can be drawn by capillary action into the fill chamber 22. The sample can flow from the fill chamber 22 and into the reaction chamber 18 because of the configuration of the immunosensor 10. Inside the reaction chamber 18 can be the first reagent 30, which can include an antibody conjugated to an enzyme in a buffer containing sucrose, poloxamers, and calcium ions, and magnetic beads 34, which can contain surface-bound antigens. Both the first reagent 30 and the magnetic beads 34 can be configured to play a role in the reaction of the sample. The antigen of the magnetic beads 34 and of the sample can block binding sites of the antibody of the first reagent 30 in a manner that prevents the conjugate of the first reagent 30 from binding to the antigen on the surface of the magnetic beads 34. After a predetermined amount of time elapses, for example two to five minutes, the adhesive tape 40 that is disposed over the vent 24 of the lower electrode 12 can be pierced. In one exemplary embodiment the meter with which the immunosensor 10 is associated with includes a piercing instrument for piercing the vent 24. Examples of a piercing instrument include a needle or other sharp tool.

The time that elapses after a sample is added to the sensor 10 but before the vent 24 is pierced can vary depending on the particular application with which the sensor 10 is used and the particular components that form the sensor 10. After a sample is introduced into the reaction chamber 18, it takes time to dissolve the reagents 30, 32. A variety of factors can affect the time it takes to dissolve the reagents 30, 32, which include, by way of non-limiting examples, the chemical make-up, viscosity, and amount of the sample with which the sensor 10 is being used, as well as the temperature of the environment within and surrounding the sensor 10. For example, blood having a high haematocrit can take longer to dissolve the reagents 30, 32 than blood having a lower red blood cell content. Likewise, it can take longer to dissolve the reagents 30, 32 at cooler temperatures.

The time it takes for the conjugate to bind to the magnetic beads 34 can also be factor that varies depending on the particular application with which the sensor 10 is used and the particular components that form the sensor 10. By way of non-limiting examples, the time it takes for the conjugate to bind to the beads 34 can depend on the viscosity of the sample, the affinity between the analyte and the antibody portion of the conjugate, and the temperature of the incubation. Typically at least some of the binding between the conjugate and the beads 34 can occur before all of the reagents 30, 32 have been dissolved.

In one exemplary embodiment, a minimum time allowed to elapse before the vent 24 is pierced can be approximately two minutes when the reaction is been carried out at approximately 37° C. In another exemplary embodiment, a minimum time allowed to elapse before the vent 24 is pierced can be approximately five minutes when the reaction is carried out at approximately 20° C. If not enough time is permitted to elapse, accuracy can be affected by there being an inadequate reaction between the antigen and the antibody. In contrast, if too much time is permitted to elapse, accuracy can be affected due to the possible evaporation of the samples as a result of the small volumes with which the sensor 10 is used. Additionally, allowing too much time to elapse is generally not preferred from a practicality standpoint—it is generally preferred to conduct the reaction as quickly as possible.

A magnet of the meter can assist in holding back the magnetic beads 34 and any antibody-enzyme conjugate that is bound to the beads from leaving the reaction chamber 18, either by exiting through the vent 24 or flowing into the detection chamber 20. The remaining portions of the conjugate can enter the detection chamber 20. In the detection chamber 20 can be the second reagent 32 on the lower electrode 12, which can include the mixture of ferricyanide, glucose, and a second mediator in an acidic buffer. The conjugate that flows from the reaction chamber 18 to the detection chamber 20 can catalyze oxidation of glucose of the second reagent 32. The oxidation of glucose can result in the formation of ferrocyanide. The presence and amount of ferrocyanide can be detected electrochemically within the detection chamber 20, which in turn can be used to calculate the concentration of the antigen in the sample. The result can be transmitted to a display mechanism in any number of ways.

One having skill in the art will recognize that although various components of the immunosensor 10 are discussed making reference to a specific material, a variety of other materials that can achieve similar results can also be used. By way of non-limiting example, although it is described that a PET sheet is sputter-coated with gold, in other embodiments a PET sheet can be sputter-coated with other metals such as palladium, platinum, iridium, silver, and mixtures thereof, or other materials that have properties that achieve similar results. Further, one skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An immunosensor, comprising:
    a lower electrode having a first liquid reagent comprising an antibody conjugated to an enzyme in a buffer, and a second liquid reagent comprising ferricyanide, a substrate for the enzyme, and an electrochemical mediator in a dilute acid solution, the first and second liquid reagents being striped on the lower electrode and then dried;
    an upper electrode having magnetic beads conjugated to an antigen striped and dried thereon;
    a separator disposed between the lower and upper electrodes;
    a reaction chamber formed in the separator and having the first reagent and the magnetic beads conjugated to the antigen disposed therein;
    a detection chamber formed in the separator and having the second reagent disposed therein;
    a fill chamber formed at least partially in the separator and one of the lower and upper electrodes, spaced a distance apart from the detection chamber, and overlapping at least a portion of the reaction chamber;
    a vent formed at least partially in each of the separator, the lower electrode, and the upper electrode, spaced a distance apart from the reaction chamber, and overlapping at least a portion of the detection chamber;
    a hydrophilic adhesive tape having an incorporated anticoagulant coupled to one of the lower and upper electrodes, disposed over the vent, and configured to form a wall of the fill chamber and seal the vent; and
    a sealing component coupled to the other of the lower and upper electrodes, disposed over the vent, and configured to seal the vent.

2. The immunosensor of claim 1, wherein the first liquid reagent comprises an antibody conjugated to glucose dehydrogenase-PQQ, and the buffer comprises citraconate, sucrose, poloxamers, and calcium ions.

3. The immunosensor of claim 1, wherein the anticoagulant comprises heparin.

4. The immunosensor of claim 3, wherein a concentration of the heparin with respect to a concentration of the hydrophilic adhesive is approximately in the range of about 0.1 to about 10 milligrams per milliliter.

5. The immunosensor of claim 1, wherein the second liquid reagent comprises ferricyanide, glucose, and phenazine ethosulfate in a dilute citraconic acid solution.

6. The immunosensor of claim 1, further comprising a meter containing a magnet disposed below the reaction chamber, the meter being configured to apply a potential between the lower and upper electrodes and to measure a resulting current.

7. The immunosensor of claim 6, further comprising a heating element associated with the meter.

8. The immunosensor of claim 6, further comprising a piercing component configured to pierce at least one of the hydrophilic tape and the sealing component disposed over the vent.

* * * * *